US010391101B2

(12) United States Patent
Zapolski et al.

(10) Patent No.: US 10,391,101 B2
(45) Date of Patent: Aug. 27, 2019

(54) DERIVATIVES OF 7-FLUORO-8-CHLORO-5H-DIBENZO [B,E,] [1,4] DIAZEPINE AND USE THEREOF

(71) Applicant: VALENTEK LLC, Moscow (RU)

(72) Inventors: Maksim E. Zapolski, Moscow (RU); Margarita A. Morozova, Moscow (RU); Allan G. Beniashvili, Moscow (RU)

(73) Assignee: VALENTEK LLC, Moscow (RU)

( * ) Notice: Subject to any disclaimer, the term of this patent is extended or adjusted under 35 U.S.C. 154(b) by 0 days.

(21) Appl. No.: 15/455,880

(22) Filed: Mar. 10, 2017

(65) Prior Publication Data

US 2017/0196883 A1 Jul. 13, 2017

Related U.S. Application Data

(63) Continuation of application No. PCT/RU2014/000939, filed on Dec. 12, 2014.

(30) Foreign Application Priority Data

Sep. 11, 2014 (RU) .............................. 2014137989

(51) Int. Cl.

| A61K 31/5513 | (2006.01) |
|---|---|
| A61K 31/5517 | (2006.01) |
| A61K 9/00 | (2006.01) |
| A61K 9/08 | (2006.01) |
| A61K 9/20 | (2006.01) |
| A61K 9/48 | (2006.01) |
| C07D 223/20 | (2006.01) |
| C07D 403/04 | (2006.01) |

(52) U.S. Cl.
CPC ........ *A61K 31/5513* (2013.01); *A61K 9/0019* (2013.01); *A61K 9/08* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2059* (2013.01); *A61K 9/48* (2013.01); *A61K 9/4858* (2013.01); *A61K 9/4866* (2013.01); *A61K 31/5517* (2013.01); *C07D 223/20* (2013.01); *C07D 403/04* (2013.01)

(58) Field of Classification Search
CPC .............. A61K 31/5513; A61K 9/2027; A61K 9/0019; A61K 9/2013; A61K 9/4858; A61K 9/2009; A61K 9/20; A61K 9/48; A61K 9/08; A61K 9/4866; A61K 9/2018; A61K 9/2059

See application file for complete search history.

(56) References Cited

U.S. PATENT DOCUMENTS

| 4,045,445 A | 8/1977 | Hardy, Jr. et al. |
| 5,538,965 A | 7/1996 | Tehim et al. |
| 5,798,350 A | 8/1998 | Tehim et al. |

FOREIGN PATENT DOCUMENTS

| RU | 2441867 C2 * | 2/2012 |
| WO | 1992/003138 A1 | 3/1992 |
| WO | 2004014895 A1 | 2/2004 |
| WO | 2008021463 A2 | 2/2008 |
| WO | 2013070107 A1 | 5/2013 |

OTHER PUBLICATIONS

Patani et al, Chem.Rev., 96, 3147-3176) (Year: 1996).*
PCT/RU2014/000939 Written Opinion and International Search Report dated Jun. 25, 2015.
Lehman, A. F. et al., Treatment of Patients with Schizophrenia, Am J Psychiatry, 2004, 161, 1-56.
Kane, J. et al., Clozapine for the Treatment-Resistant Schizophrenic, Arch Gen Psychiatry, 1988, vol. 45, 789-96.
Wahlbeck, K. et. al.,Clozapine versus typical neuroleptic medication for schizophrenia, Cochrane Database Syst Rev, 2000, CD000059.
Rosenheck, R. et. al., How Long to Wait for a Response to Clozapine: A Clozapine of Time Course of Response to Clozapine and Conventional Antipsychotic Medication in Refractiory Schizophrenia: Schizophr Bull, 1999, 25, 709-19.
Spina, E. et. al., Relationship between plasma concentrations of colozapine and norclozapine and therapeutic response in patients with schizophrenia resistant to conventional neuroleptics, Psychopharmacology (Berl), 2000, 148, 83-9.
Alvir, J. M. et al., Clozapine Induced Agranulocytosis, N Engl J Med, 1993, 329, 162-7.
Guest, I. et. al., Drugs that Induce Neutropenia/Agranulocytosis May Target Specific Components if the Stromal Cell Extracelluar Matirx, Med Hypotheses, 1999, 53, 145-51.
Williams, D. P. et. al., Neutrophil Cytotoxicity of the Chemically Reactive Metabolite(s) of Clozapine: Possible Role in Agranulocytosis, J Pharmacol Exp Ther, 1997, 283, 1375-82.
Liu, Z. C. et. al., Clozapine is Oxidized by Activated Human Neutrophils to a Reactive Nitrenium Ion that Irreversibly Binds to the Cells, J Pharmacol Exp Ther, 1995, 275, 1476-83.
Dain, J. G. et al., Biotransformation of Clozapine in Humans, Drug Metab Dispos, 1997, 25, 603-9.
Schaber, G. et al., Isolation and Identification of Clozapine Metabolites in Patient Urine, Drug Metab Dispos, 2001, 29, 923-31.
Iverson, S. et. al., Effect of Clozapine on Neutrophil Kinetics in Rabbits, Chem Res Toxicol, 2010, 23, 1184-91.

(Continued)

*Primary Examiner* — Sudhakar Katakam
(74) *Attorney, Agent, or Firm* — Arent Fox LLP; Michael Fainberg (57) ABSTRACT

This present disclosure generally relates to medicine, and in particular to pharmacology and psychiatry, and discloses active agents and related methods of treatment which can be used for the treatment of treatment-resistant forms of schizophrenia. In some exemplary aspects, such treatments allow for eliminating both the positive and negative symptoms of schizophrenia, and cognitive disorders, without causing severe side effects that limit their use, such as sedation, tachycardia, orthostatism, agranulocytosis and sialorrhea.

8 Claims, 8 Drawing Sheets

(56) References Cited

OTHER PUBLICATIONS

Ng, W. et. al., Effect of Aminoglutothimide on Neutrophils in Rats: Implications for Idiosyncratic Drug-Induced Blood Dyscrasis, Chem Res Toxicol, 2013, 26, 1272-81.
Leucht, S. et. al., Comparative efficacy and tolerability of 15 antipsychotic drugs in schizophrenia: a multiple-treatments meta-analysis, Lancet, 2013, 382, 951-62.
Ben-Aryah, H. et. al., Salivary Flow-Rate and Composition in Schizophrenic Patients on Clozapine: Subjective Reports and Laboratory Data, Biol Psychiatry, 1996, 39, 946-9.
Knable, M. B. et. al., Extrapyramidal side-effects with risperidone and haloperidol at comparable D2 receptor occupancy levels,Psychiatry Res, 1997, 75, 91-101.
Fisher, A., Cholinergic Treatments with Emphasis on M1 Muscarinic Agonists as Potential Disease-Modifying Agents for Alzheimer's Disease, Neurotherapeutics, 2008, 5, 433-42.
Shekhar, A. et. al., Selective Muscarinic Receptor Agonist Xanemoline as a Novel Treatment Approach for Schizophrenia, Am J Psychiatry, 2008, 165, 1033-9.
Bubeníková, Věra, et al. "The effect of zotepine, risperidone, clozapine and olanzapine on MK-801-disrupted sensorimotor gating." Pharmacology Biochemistry and Behavior 80.4 (2005): 591-596.
Swerdlow, Neal R., Daniel Zisook, and Navid Taaid. "Seroquel (ICI 204,636) restores prepulse inhibition of acoustic startle in apomorphine-treated rats: Similarities to clozapine." Psychopharmacology 114.4 (1994): 675-678.
Dragovic, Sanja, et al. "Role of human glutathione S-transferases in the inactivation of reactive metabolites of clozapine." Chemical research in toxicology 23.9 (2010): 1467-1476.
Chapelle, Albert, et al. "Clozapine-induced agranulocytosis." Human genetics 37.2 (1977): 183-194.
Gerson, Stanton L., and Herbert Meltzer. "Mechanisms of clozapine-induced agranulocytosis." Drug Safety 7.1 (1992): 17-25.
Jann, Michael W., et al. "Pharmacokinetics and pharmacodynamics of clozapine." Clinical pharmacokinetics 24.2 (1993): 161-176.
Rosenthaler, Joachim, et al. "Non-equilibrium Method for the Radioimmunoassay of Clozapine in the Presence of Metabolites." The FEBS Journal 80.2 (1977): 603-609.
Schaber, Gisela, et al. "Isolation and identification of clozapine metabolites in patient urine." Drug Metabolism and Disposition 29.6 (2001): 923-931.
Dain, Jeremy G., Joseph Nicoletti, and Frances Ballard. "Biotransformation of clozapine in humans." Drug metabolism and disposition 25.5 (1997): 603-609.
Williams, Dominic P., et al. "Neutrophil cytotoxicity of the chemically reactive metabolite (s) of clozapine: possible role in agranulocytosis." Journal of Pharmacology and Experimental Therapeutics 283.3 (1997): 1375-1382.
Hasegawa, Mitsuru, Philip A. Cola, and Herbert Y. Meltzer. "Plasma clozapine and desmethylclozapine levels in clozapine-induced agranulocytosis." Neuropsychopharmacology 11.1 (1994): 45.
Williams, Dominic P., et al. "Neutrophil cytotoxicity of the chemically reactive metabolite (s) of clozapine: possible role in agranulocytosis." Journal of Pharmacology and Experimental Therapeutics 283.3 (1997).
Mason, Ronald P., and Volker Fischer. "Possible role of free radical formation in drug-induced agranulocytosis." Drug safety 7.1 (1992): 45-50.
Frimat, B., et al. "Metabolism of clozapine by human neutrophils: evidence for a specific oxidation of clozapine by the myeloperoxidase system with inhibition of enzymatic chlorination cycle." Fundamental & clinical pharmacology 11.3 (1997): 267-274.
Pirmohamed, Munir, and Kevin Park. "Mechanism of clozapine-induced agranulocytosis." CNS drugs 7.2 (1997): 139-158.
Tschen, Alice C., et al. "The cytotoxicity of clozapine metabolites: Implications for predicting clozapine-induced agranulocytosis." Clinical Pharmacology & Therapeutics 65.5 (1999): 526-532.
Williams, Dominic P., et al. "Induction of metabolism-dependent and-independent neutrophil apoptosis by clozapine." Molecular pharmacology 58.1 (2000): 207-216.
Maggs, James L., et al. "The metabolic formation of reactive intermediates from clozapine, a drug associated with agranulocytosis in man." Journal of Pharmacology and Experimental Therapeutics 275.3 (1995): 1463-1475.
Pirmohamed, Munir, et al. "Metabolism and bioactivation of clozapine by human liver in vitro." Journal of Pharmacology and Experimental Therapeutics 272.3 (1995): 984-990.
Loeffler, S., et al. "Increased apoptosis of neutrophils in a case of clozapine-induced agranulocytosis." Pharmacopsychiatry 36.01 (2003): 37-4.
Iverson, S., N. Zahid, and J. P. Uetrecht. "Predicting drug-induced agranulocytosis: characterizing neutrophil-generated metabolites of a model compound, DMP 406, and assessing the relevance of an in vitro apoptosis assay for identifying drugs that may cause agranulocytosis." Chemico-biological interactions 142.1-2 (2002): 175-199.
Lieberman, Jeffrey A., et al. "HLA-B38, DR4, DQw3 and clozapine-induced agranulocytosis in Jewish patients with schizophrenia." Archives of general psychiatry 47.10 (1990): 945-948.
Lieberman, Jeffrey A., et al. "Clozapine-induced agranulocytosis: non-cross-reactivity with other psychotropic drugs." The Journal of clinical psychiatry (1988).
Pfister, G. M., et al. "Clozapine-induced agranulocytosis in a Native American: HLA typing and further support for an immune-mediated mechanism." The Journal of clinical psychiatry 53.7 (1992): 242-244.

\* cited by examiner

DERIVATIVES OF 7-FLUORO-8-CHLORO-5H-DIBENZO [B,E,] [1,4] DIAZEPINE AND USE THEREOF

CROSS-REFERENCE TO RELATED APPLICATIONS

This application is a continuation application that claims priority to International Patent Application No. PCT/RU2014/000939, filed on Dec. 12, 2014, which claims priority to Russian Federation Application No. 2014137989, filed on Sep. 11, 2014, the contents of each of which is incorporated herein by reference.

TECHNICAL FIELD

The invention relates to medicine, in particular to pharmacology and psychiatry, and can be used for manufacturing of medications for therapy of treatment-resistant forms of schizophrenia.

BACKGROUND

At present, the mental health is one of the most serious challenges all countries have to deal with, since at least every fourth person faces such problems during a lifetime. Prevalence of mental health disorders in the European Region is very high. According to the WHO (2006), about 4 of 870 million people in the European Region suffer from schizophrenia; 4 million—from bipolar affective disorders, and 4 million—from panic disorders.

Mental disorders represent the second (after cardiovascular diseases) major cause of disease burden. Their share takes up to 19.5% of DALYs (disability-adjusted life years). More than 40% of all chronic diseases are mental disorders.

The first drugs used for the medication-assisted treatment of schizophrenia—so called typical antipsychotic agents, such as haloperidol, chlorpromazine, etc.—involve a high rate of CNS side effects (convulsions, tardive dyskinesia, akathisia), cardiovascular side effects (arrhythmia, orthostatic hypotension) and endocrine side-effects (weight gain). Motor and movement disorders resulting from the intake of typical antipsychotic agents are often permanent, so their use in treatment of schizophrenia and bipolar disorder is limited and the need to reduce the number of side effects was the main motivator for the development of antipsychotics of new generation. Clozapine (I) developed in the 1960s was the first among such medications. Thereafter both in clinical trials and in the market other atypical antipsychotics appeared. They were dibenzodiazepine derivatives olanzapine (II) and quetiapine (III), as well as compounds of other structural classes: risperidone (IV), ziprasidone (V), aripiprazole (VI).

(I)

(II)

(III)

(IV)

(V)

VI)

However, according to various authors, from 5 to 30% of schizophrenic patients are resistant to treatment with conventional antipsychotics, which have limited therapeutic options. The problem of therapeutically-resistant schizophrenia is one of the most important problems in the modern psychiatry.

Treatment resistance may be defined as little or no symptomatic response to multiple (at least two) antipsychotics of different pharmacological classes in average or maximum permissible doses within 6-8 weeks (Lehman, A. F. et. al., Am J Psychiatry, 2004, 161, 1-56).

Based on analysis of data on clinical predictors of drug resistance, a number of authors have described its various types, which is very important from a practical standpoint. It has been proposed to distinguish between resistance to antipsychotic treatment, which is observed since therapy commencement (anticipated low curability, primary resistance), and resistance emerging in the course of treatment (anticipated insufficient curability, adaptation to psychotropic effects of neuroleptics, secondary resistance). Current reinterpretation of this differentiation suggests that the primary resistance is observed under the initial "malignant" course of endogenous process (pubescent insanity, continuous progressive course). The secondary resistance has syndromological basis to a greater extent. In this case, the "non-response" to therapy is associated with the emergence of complex of deep-rooted symptoms (chronic delusions, various positive disorders in the structure of disorder, diminished symptoms), rather than with the peculiarities of schizophrenia.

The pathological mechanisms of resistance to antipsychotic therapy have not been determined yet. Aside from fewness, contratiety and fragmentation of the data obtained, this can also be explained with the lack of a clear understanding of complicated pathogenesis of schizophrenia. The role of features of abnormalities in different elements of neurotransmitter systems in various brain regions (pharmacodynamic factor), immunological and endocrine factors is being discussed. The significance of features of individual pharmacokinetics, for example, reduction of bioavailability (and, therefore, antipsychotic activity) of neuroleptic due to the individual features of absorption processes, metabolism and excretion, should not be underestimated. A major role in the formation of resistance belongs to genetic factors, which form the basis of pharmacodynamic and pharmacokinetic features of resistant patients. For example, the importance of genes responsible for the formation and functioning of dopamine, serotonin and other receptors; genes of enzymes that destroy neurotransmitters; genes of cytochrome P450 enzymes; genes of drug transporter proteins.

The choice of therapeutic tactics in case of resistance to antipsychotic therapy is extremely difficult. Various drug and non-drug methods of treatment for treatment-resistant forms of schizophrenia have been proposed. These are clozapine therapy, electroconvulsive therapy, proceeding to the therapy with a typical neuroleptic, proceeding to the therapy with an atypical neuroleptic, use of high and ultra-high doses of neuroleptics, temporary withdrawal (cessation) of antipsychotic therapy, combination of several neuroleptics, combination of antipsychotic and forced insulin shock therapy, and other methods.

Special attention should be paid the data on high efficiency of atypical neuroleptic clozapine in the treatment of schizophrenic patients resistant to antipsychotic therapy. Its efficiency has been proved in the very first large-scale trial (Kane, J. et. al., *Arch Gen Psychiatry*, 1988, 45, 789-96) and then has been repeatedly confirmed thereafter. It has been proven in precisely designed trials, the methodology of which is fully consistent with the principles of evidence-based medicine (Wahlbeck, K. et. al., *Cochrane Database Syst Rev*, 2000, CD000059). The number of patients with significant improvements due to administration of clozapine is about twice the number for traditional neuroleptics. It is believed that the clozapine therapy weakens positive symptoms of 30-60% of patients resistant to typical neuroleptics. Clozapine is recognized as the only antipsychotic agent, efficiency of which in resistant cases has been proven. There are certain controversies as to the timing of onset of therapeutic effect with clozapine in resistant cases of schizophrenia. According to some estimates, the condition of patients can be improved within a few months (Rosenheck, R. et. al., *Schizophr Bull*, 1999, 25, 709-19). Results of other trials evidence more extended time frames of onset of therapeutic effect (Spina, E. et. al., *Psychopharmacology (Berl)*, 2000, 148, 83-9). Regardless, clozapine is the only neuroleptic officially recommended for use in case of resistance to other antipsychotic agents. At the same time it should be noted that clozapine is recommended both in case of in primary and secondary forms of resistance.

In case of long-term use, clozapine allows for improvement of condition of 60% of patients suffering from treatment-resistant forms of schizophrenia. Clozapine eliminates both the positive symptoms of schizophrenia (delusion, auditory hallucinations, thought disorders) and negative symptoms (flat affect, poverty of speech) and cognitive impairments.

The main disadvantage of clozapine, due to which the medication was recalled from the market in some countries in 1975, is the risk of agranulocytosis, a life-threatening condition, which entails decrease in the number of leukocytes and neutrophils in the blood. The probability of agranulocytosis occurrence among patients taking clozapine reaches 0.8% (Alvir, J. M. et. al., *N Engl J Med*, 1993, 329, 162-7), and 3-4% of them die. The use of clozapine for the treatment of some forms of schizophrenia was again permitted upon condition of weekly monitoring of the count of leukocytes and neutrophils in the blood. Because of the risk of agranulocytosis, clozapine is used only in cases when the use of other medications is ineffective. In addition, clozapine is difficult to administer due to frequent cases of autonomic dysfunction (tachycardia, orthostatism, sialorrhea, constipation) and significant sedation.

Despite many years of attempts to develop a safer and more effective agent for the treatment of schizophrenia, none of them had better efficacy than clozapine, the best atypical antipsychotic in its class. At the same time, the risk of tachycardia, orthostatism, sedation and agranulocytosis imposes substantial limitations on the clinical use of clozapine.

SUMMARY

The present disclosure provides a new medication to treat treatment-resistant forms of schizophrenia with efficacy at least equal to efficacy of clozapine, but without severe side effects.

In some aspects, the technical result achieved using the invention is the synthesis of an effective medication for treatment of treatment-resistant forms of schizophrenia, which may result in the elimination of both the positive symptoms of schizophrenia (including delusion, auditory hallucinations, thought disorder) and its negative symptoms (including flat affect, poverty of speech), as well as cognitive disorders. The active agents disclosed herein are also notable for the fact that they may be administered in a manner which does not cause severe side effects that limit their use, including sedation, tachycardia, orthostatism, agranulocytosis and hypersalivation.

This technical result, and other benefits which will be apparent in light of the disclosure, are achieved through the use of 11-(4-methyl piperazine-1-yl)-7-fluoro-8-chloro-5H-dibenzo[b,e][1,4]diazepine (hereinafter, "fluoroclozapine," "FClo," or "FC") or 11-(piperazine-1-yl)-7-fluoro-8-chloro-5H-dibenzo[b,e][1,4]diazepine (hereinafter, "desmethylfluoroclozapine," "dFClo," or "DMFC") or pharmaceutically acceptable salt, hydrate or solvate of one of these compounds for the therapy of treatment-resistant forms of schizophrenia.

Thus, according to one aspect of the disclosure it is proposed to use 11-(piperazine-1-yl)-7-fluoro-8-chloro-5H-dibenzo[b,e][1,4]diazepine, 11-(4-methyl piperazine-1-yl)-

7-fluoro-8-chloro-5H-dibenzo[b,e][1,4]diazepine, or pharmaceutically acceptable salt, hydrate or solvate of one of these compounds for the synthesis of a medication for therapy of treatment-resistant forms of schizophrenia.

Another aspect of the disclosure is a pharmaceutical composition for therapy of treatment-resistant forms of schizophrenia, containing 11-(piperazine-1-yl)-7-fluoro-8-chloro-5H-dibenzo[b,e][1,4]diazepine or 11-(4-methyl piperazine-1-yl)-7-fluoro-8-chloro-5H-dibenzo[b,e][1,4]diazepine, or a pharmaceutically acceptable salt, hydrate or solvate of one of these compounds as an active ingredient in a therapeutically effective amount.

In some exemplary aspects, the pharmaceutical composition contains 50 to 600 mg of active ingredient.

In some exemplary aspects, the pharmaceutical composition contains one or more ingredients listed below: lactose (sugar of milk); starch; polyvinyl pyrrolidone (povidone); colloidal silicon dioxide (aerosil); magnesium stearate; talc; lauric acid; hydroxyanisole; and/or vegetable oil.

In some exemplary aspects, the pharmaceutical composition contains from 0.5 to 99.9% of active ingredient.

Some exemplary aspectsrelate to pharmaceutical compositions in the form of tablets, capsules, solutions for injection, sprays, transdermal therapeutic systems or suppositories.

BRIEF DESCRIPTION OF THE DRAWINGS

FIG. 4 provides a chart that illustrates the effect of clozapine (FIG. 4A) and fluoroclozapine (FIG. 4B) on reduction on prepulse inhibition induced by intake of ketamine. The dependence of percentage of inhibition on prepulse intensity (in dB) for the various doses of test medications, positive control (Control) and a negative control (Ketamine).

DETAILED DESCRIPTION

According to one aspect of the disclosure, the treatment-resistant forms of schizophrenia (schizophrenia resistant to antipsychotic therapy) are understood as cases of slight decline in the severity of positive disorders and cases of complete absence of improvement in the patient's condition after sequential treatment with two neuroleptics (antipsychotics) of different pharmacological classes in average or maximum permissible doses within 6-8 weeks. At that, neuroleptics (antipsychotics) are understood, in particular, as treatment with olanzapine, quetiapine, haloperidol, risperidone, zuclopenthixol, perphenazine.

Non-limiting examples of types and subtypes of schizophrenia, for the treatment of resistant forms of which the invention is intended, are paranoid, disorganized, catatonic, undifferentiated and residual types of schizophrenia, schizophrenoform disorder, schizoaffective disorder, or schizotypal disorder.

Examples of resistance that limits the use of existing antipsychotic drugs is the resistance associated with the failure to form a remission, or to achieve the expected therapeutic response, or to achieve a therapeutic response due to severe side effects, particularly, when the use of antipsychotic drugs is limited due to the emergence or worsening of side effects associated with the medication.

Side effects limiting the use of antipsychotic drugs include agranulocytosis, sedation, cognitive disorders, such as disorder of attention or of different aspects of memory, manifestations of autonomic dysfunction, such as tachysystole, orthostatism, accommodation disorder, dysfunction of gastrointestinal tract and urination, weight gain, behavioral toxicity, such as lack of coordination of muscle movements, absent-minded behavior, drowsiness episodes, drooling.

The term "pharmaceutically acceptable salts" used herein includes salts of active compounds which have been prepared with relatively non-toxic acids or bases. Examples of pharmaceutically acceptable non-toxic salts include salts formed with inorganic acids, such as hydrochloric, hydrobromic, phosphoric, sulfuric and perchloric acid, or with organic acids, such as acetic, oxalic, maleic, tartaric, succinic, citric or malonic acid, or formed by other methods used in the art, for example by means of ion exchange. Other pharmaceutically acceptable salts include adipate, alginate, ascorbate, aspartate, benzene sulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanate, hexanoate, hydroiodide, 2-hydroxy-ethanesulfonate, lactobionate, lactate, laurate, lauryl sulfate, malate, maleate, malonate, methanesulfonate (mesylate), 2-naphthalenesulfonate, nicotinate, nitrate, oleate, oxalate, palmitate, pamoate, pectinate, persulfate, 3-phenylpropionate, phosphate, picrate, pivalate, propionate, hemifumarate, stearate, succinate, sulfate, tartrate, thiocyanate, p-toluenesulfonate (tosylate), undecanoate, valerate, and the like.

The term "solvate" is understood as an association or complex of one or more molecules of solvent and a compound according to the invention. Examples of solvents that form solvates include, without limitation, water, isopropanol, ethanol, methanol, DMSO, ethyl acetate, acetic acid and ethanolamine. The term "hydrate" refers to a complex where the molecule of solvent is water.

The invention also relates to pharmaceutical compositions which contain at least one of the compounds described herein (or a pro-drug, a pharmaceutically acceptable salt or other pharmaceutically acceptable derivative) and one or more pharmaceutically acceptable carriers, solvents and/or excipients. These compositions may also contain one or more additional therapeutic agents. Furthermore, the compound of the invention may be administered to a patient in need of appropriate therapy, in combination with one or more other therapeutic agents.

Pharmaceutical compositions according to this disclosure may contain one or more active compounds together with pharmaceutically acceptable carriers that may include any solvents, diluents, dispersions or suspensions, surfactants, isotonic agents, thickeners and emulsifiers, preservatives, binding agents, lubricants, etc., suitable for the particular dosage form. Except for cases, when the medium of conventional carriers is incompatible with the invention compound, for example, upon occurrence of any undesirable biological effects or other adverse interactions with any other component(s) of the pharmaceutical composition, the use of such compositions falls within the scope of this invention. Materials that can serve as pharmaceutically acceptable carriers include, without limitation, mono- and oligosaccharides and the derivatives thereof; malt; gelatin; talc; excipients, such as cocoa butter and suppository waxes; oils, such as peanut oil, cottonseed oil, safflower oil, sesame oil, olive oil, corn oil and soybean oil; glycols such as propylene glycol; esters, such as ethyl oleate and ethyl laurate; agar; buffering agents, such as magnesium hydroxide and aluminum hydroxide; alginic acid; pyrogen-free water; isotonic saline, Ringer's solution; ethyl alcohol and phosphate buffer solutions. In addition, the composition may contain other non-toxic compatible lubricants, such as sodium lauryl sulfate and magnesium stearate, as well as coloring agents, parting fluids, film formers, sweeteners, flavoring and perfuming agents, preservatives and antioxidants.

Dosage forms, a class of pharmaceutical compositions, the formula of which is optimized for a particular route of administration in a therapeutically effective dose, are also the subject matter of the invention. Medical compositions of this invention allow for the following routes of administration: oral, topical, intrarectal, intraocular, pulmonary (for example, in the form of spray for inhalation) or intravascular, intranasal, intraperitoneal, subcutaneous, intramuscular, intrasternal, transdermal and infusional administration according to recommended dosages.

Dosage forms according to the disclosure may contain a compound of any formula described herein, or a pharmaceutically acceptable salt, solvate or hydrate thereof, and any pharmaceutically acceptable carrier, adjuvant or solvent. The term "pharmaceutically acceptable carrier or adjuvant" means a carrier or adjuvant that may be administered together with any of the active compounds disclosed herein and which does not destroy the pharmacological activity of this compound and is non-toxic when administered at doses sufficient to deliver a therapeutic amount of the compound.

Dosage forms according to the disclosure may contain compositions prepared by means of the use of liposomes or methods of microencapsulation, methods of preparing drug nanoparticles and other examples, which are known in the pharmaceutics.

Figure 6:
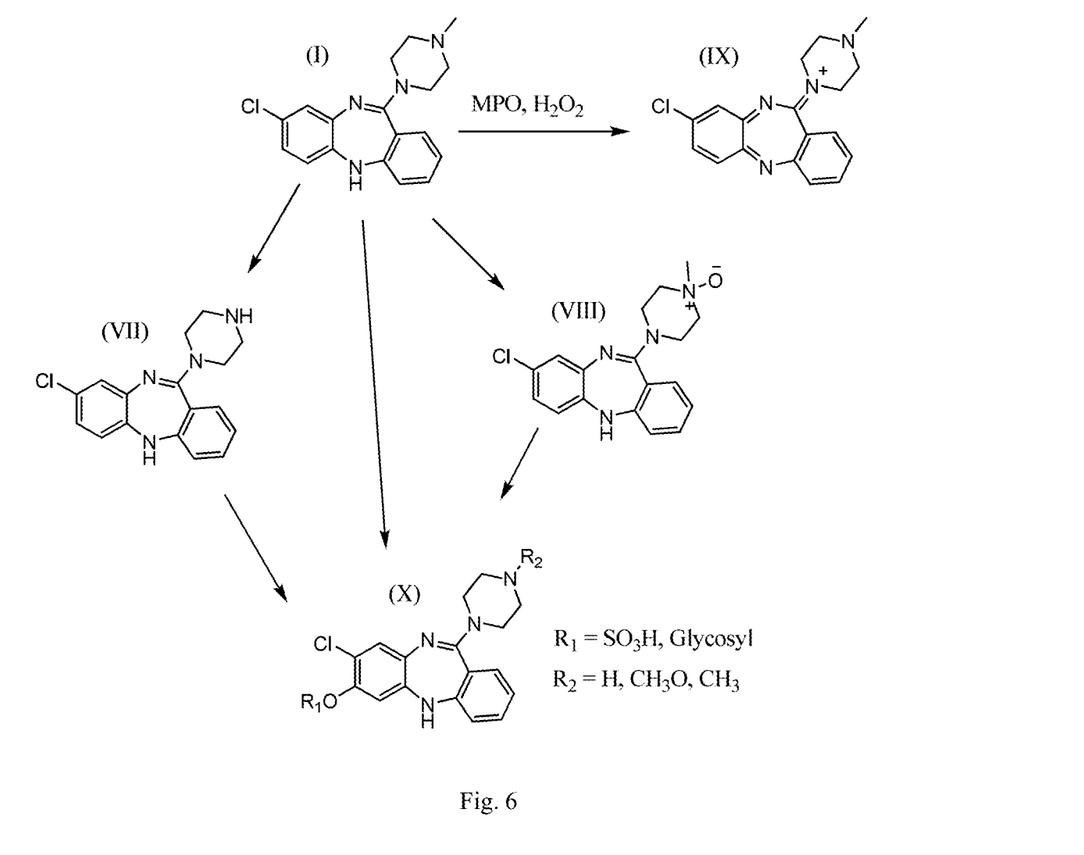
FIG. 6 provides a flowchart illustrating selected reactions involving clozapine and its metabolites.

According to modern concepts, the main cause of agranulocytosis is the formation of toxic metabolites of the compounds under the effect of myeloperoxidase, an enzyme produced by activated neutrophils during an inflammatory response and responsible for the formation of hypochlorous acid (Guest, I. et. al., Med Hypotheses, 1999, 53, 145-51). Neither clozapine (I) nor its main stable metabolites, clozapine N-oxide (VIII) and N-desmethylclozapine (VII), are toxic per se (Williams, D. P. et. al., J Pharmacol Exp Ther, 1997, 283, 1375-82). However, oxidation of clozapine, when exposed to hydrogen peroxide and myeloperoxidase leads to the formation of nitrene clozapine (IX), an extremely reactive compound, the toxicity of which is caused by the ability to irreversibly bind to macromolecules of cells (Liu, Z. C. et. al., J Pharmacol Exp Ther, 1995, 275, 1476-83). Exemplary reactions and conversions involving clozapine and its metabolites are illustrated by FIG. 6.

The exact mechanism of clozapine oxidation has not been determined yet: in the presence of saturating concentrations of glutathione, the positions 6 and 9 of the benzene ring appear to be the most reactive (Williams, D. P. et. al., J Pharmacol Exp Ther, 1997, 283, 1375-82). On the other hand, studies of clozapine metabolites produced in vivo have shown that the most common metabolic pathways include the hydroxylation for position 7 and the formation of compounds (X) (Dain, J. G. et. al., DrugMetab Dispos, 1997, 25, 603-9; Schaber, G. et. al., Drug Metab Dispos, 2001, 29, 923-31).

In the compounds fluoroclozapine (XI) and desmethylfluoroclozapine (XII), hydrogen atom bonded to the carbon atom at position 7 is substituted by fluorine.

Following our research it has unexpectedly been found that the introduction of fluorine into position 7 of molecules of clozapine and N-desmethylclozapine prevents the formation of their toxic metabolites in vivo. Most likely, a substantial reduction in toxicity occurs because introduction of fluorine into position 7 allows avoiding the most probable path of oxidation of benzodiazepine nucleus in vivo. Furthermore, acceptor properties of the substituent reduce the reactivity of nitrene ion and, consequently, lead to the reduction in toxicity of the oxidation products of compounds and the metabolites thereof in comparison with clozapine and N-desmethylclozapine.

The use of effective atypical antipsychotics, such as clozapine, quetiapine, risperidone, olanzapine, etc., involves the risk of undesirable side effects due to the ability of active components to bind to signaling receptors that are not the main targets.

The side effects caused by binding to signaling receptors include sedation, cognitive disorders (disorder of attention or different aspects of memory), manifestations of autonomic dysfunction (tachysystole, orthostatism, accommodation disorder, dysfunction of gastrointestinal tract and urination), weight gain, behavioral toxicity (lack of coordination of muscle movements, absent-minded behavior, drowsiness episodes).

Pre-clinical and clinical trials of selective ligands of G-protein-coupled receptors (GPCR) allow relating the side effects to the influence on the individual receptors. Following the functional studies on receptor panels in vitro, it has been found that the introduction of fluorine atom substantially modifies the interaction with histamine, muscarinic and dopamine receptors, which significantly reduces the risk of a number of direct side effects that limit the use of clozapine.

At the same time, our research has unexpectedly shown that the introduction of fluorine atom into position 7 of clozapine molecule and of its active metabolite desmethylclozapine, does not adversely affect the unique clinical efficacy inherent only in clozapine, allowing to use it in treatment of treatment-resistant forms of schizophrenia, while research teams that have tried to modify clozapine following other, often multiple, directions, failed to do the same.

The possibility of objective demonstration of the technical result while using the invention has been confirmed by reliable data outlined in the examples and containing the experimental data obtained in the process of research following the procedures recognized in the art. This aspect of the invention is also illustrated with drawings.

Example 1

Reducing the Risk of Agranulocytosis

The positive effect of the introduction of fluorine has been observed in pre-clinical studies of sub-chronic toxicity. Currently, neither reliable method to predict the risk of agranulocytosis taking into account the haematological toxicity in vitro nor animal model of agranulocytosis induced by clozapine exist. It is known that the administration of clozapine to rabbits leads to increase in neutrophil release from the bone marrow and to a reduction in the time neutrophils remain in circulation (Iverson, S. et. al., *Chem Res Toxicol*, 2010, 23, 1184-91). This effect is similar to neutropenia, which is manifested in many patients at the beginning of clozapine therapy, and in most cases does not progress to its severe form—agranulocytosis. Increase in the number of neutrophils has been observed among rats after administration of aminoglutethimide, which also involves a high risk of agranulocytosis (Ng, W. et. al., *Chem Res Toxicol*, 2013, 26, 1272-81). Thus changes in the kinetics of neutrophils after intake of the medication can serve as a biomarker to predict the risk of agranulocytosis.

The neutrophil kinetics has been studied within comparative tests of sub-chronic toxicity. Studies have been conducted using rats upon intragastric administration of the substance at a dose of 5 mg/kg. The test substances were administered daily for 28 days. Each experimental group was composed of 10 animals of each sex.

Analysis of morphological parameters of blood of the animals from experimental groups revealed a significant increase in the number of circulating neutrophils in the blood of rats treated with clozapine. The number of neutrophils in the peripheral blood of rats treated with fluoroclozapine and desmethylfluoroclozapine, did not differ so much different from that of the control group.

|  | Control | FClo 5 mg/kg | dFClo 5 mg/kg | Clozapine 5 mg/kg |
|---|---|---|---|---|
| Hemoglobin, g/l | 156.0 ± 2.5 | 155.4 ± 2.1 | 153.4 ± 2.4 | 154.6 ± 1.9 |
| RBC count $10^{12}$/l | 8.39 ± 0.06 | 8.43 ± 0.07 | 8.35 ± 0.07 | 8.39 ± 0.06 |
| Ht, % | 43.3 ± 0.7 | 43.2 ± 0.7 | 42.5 ± 0.5 | 43.3 ± 0.5 |
| MCV, fl | 51.6 ± 0.5 | 51.3 ± 0.5 | 50.9 ± 0.2 | 51.6 ± 0.2 |
| MCH, pg | 18.6 ± 0.2 | 18.4 ± 0.1 | 18.4 ± 0.1 | 18.4 ± 0.1 |
| MCHC, g/l | 360.2 ± 4.0 | 359.4 ± 1.9 | 360.8 ± 2.2 | 357.4 ± 1.9 |
| Rt, $10^9$/l | 81.6 ± 3.6 | 77.6 ± 4.6 | 75.6 ± 3.1 | 80.8 ± 4.1 |
| ESR, mm/h | 3.0 ± 0.3 | 4.2 ± 0.4 | 4.2 ± 0.4 | 3.8 ± 0.4 |
| PLT count, $10^9$/l | 682.6 ± 28.5 | 666.4 ± 26.0 | 653.4 ± 29.8 | 617.6 ± 43.2 |
| WBC count, $10^9$/l | 11.5 ± 1.2 | 11.2 ± 0.8 | 11.7 ± 0.9 | 11.6 ± 1.1 |
| Myelocytes, % | 0.0 ± 0.0 | 0.0 ± 0.0 | 0.0 ± 0.0 | 0.0 ± 0.0 |
| Metamyelocytes, % | 0.0 ± 0.0 | 0.0 ± 0.0 | 0.0 ± 0.0 | 0.0 ± 0.0 |
| Stab neutrophiles, % | 2.4 ± 0.5 | 3.2 ± 0.4 | 4.2 ± 0.4 | 4.6 ± 0.7* |
| Segmented neutrophils, % | 20.4 ± 2.1 | 20.8 ± 1.5 | 21.4 ± 1.7 | 21.2 ± 2.0 |
| Basophils, % | 0.8 ± 0.4 | 1.0 ± 0.3 | 0.6 ± 0.3 | 0.6 ± 0.3 |
| Eosinophils, % | 0.8 ± 0.4 | 0.8 ± 0.4 | 1.0 ± 0.5 | 1.0 ± 0.5 |
| Monocytes, % | 6.6 ± 0.9 | 6.4 ± 0.5 | 6.2 ± 1.0 | 6.4 ± 0.9 |
| Lymphocytes % | 69.0 ± 3.0 | 67.8 ± 2.4 | 66.6 ± 2.8 | 66.6 ± 2.8 |
| Plasma cells, % | 0.0 ± 0.0 | 0.0 ± 0.0 | 0.0 ± 0.0 | 0.0 ± 0.0 |

Thus, the introduction of the fluorine substituent into benzodiazepine nucleus reduces the risk of agranulocytosis due to blocking the pathways leading to the formation of toxic metabolites.

Example 2

Decreasing Sedation

Sedation is a common side effect of antihistamines—antagonists of H1 histamine receptor penetrating through the blood-brain barrier. Sedation is a reason to use antihistamines—diphenhydramine and doxylamine as medications against insomnia. Sedation due to the effect on histamine receptors is a side effect of most antipsychotic drugs. For example, intake of clozapine increases the risk of sedation by 8.8 times, intake of olanzapine—by 3.3 times, intake of quetiapine—by 3.7 times (Leucht, S. et. al., *Lancet*, 2013, 382, 951-62). Reducing the binding to H1 receptors was a motivation for the development of new antipsychotic drugs (application PCT/IB2003/003583, Eli Lilly And Company, publ. on Feb. 19, 2004).

It is known from the prior art that desmethylfluoroclozapine binds to histamine receptors (application PCT/RU2011/000869, OOO Valentek, publ. on May 16, 2013). However, it is not possible to compare the bond strength of clozapine, norclozapine and fluorinated analogues thereof according to the data presented in the application, because even in concentration of 1 μM the receptor blockade close to 100% was observed. In addition, the disclosed information referred only to the strength of interaction between molecules of ligand and receptor and did not allow making any conclusions in regard to the cell-mediated response as a result of such interaction. It is known that in some circumstances, the ligand binding to the receptor may activate the signaling pathway or not activate the receptor and thus block the effect of endogenous activator or activate the signaling pathway different from that activated by the endogenous ligand.

The interaction of fluoroclozapine (FClo) desmethylfluoroclozapine (dFClo), clozapine (Clo) and desmethylclozapine (dClo) with histamine receptors was studied in the functional experiments. The functional activity of compounds on the H4 receptor was determined according to the change in the cell conductibility induced by redistribution of intracellular calcium. The activity for H1 receptor was determined according to the fluorescence of Fluo-4 NW indicator introduced into cells induced by the change in Ca2+ ion concentration in the cytosol.

Functional experiments were performed in the set-up of agonism and antagonism. In the set-up of agonism the test substance was added directly to the cells expressing the receptor and was determined as the dependence of the response intensity on the substance concentration. Concentration at which the half-peak response (EC50) could be reached served as a measure of activity of agonists.

In the set-up of antagonism, the ability of test substances to block the action of agonists was assessed. For this purpose, cells were incubated with the test substances, then the reference agonists were added in the system and the functional response was determined. The concentration at which the response to the agonist was blocked by 50% ($IC_{50}$), served as a measure of activity of antagonists.

|    | Antagonism ($IC_{50}$, µM) | | | | Agonism ($EC_{50}$, µM) | | | |
|----|-------|-------|-------|--------|-------|------|------|------|
|    | dFClo | dClo  | FClo  | Clo    | dFClo | dClo | FClo | Clo  |
| H1 | 0.061 | 0.015 | 0.018 | 0.0059 |       |      |      |      |
| H4 |       |       |       |        | 2     | 2.1  | 0.17 | 0.14 |

The study unexpectedly revealed that fluoroclozapine and desmethylfluoroclozapine blocked the H1 receptor much weaker and thus presumably caused lower sedation.

Figure 1:
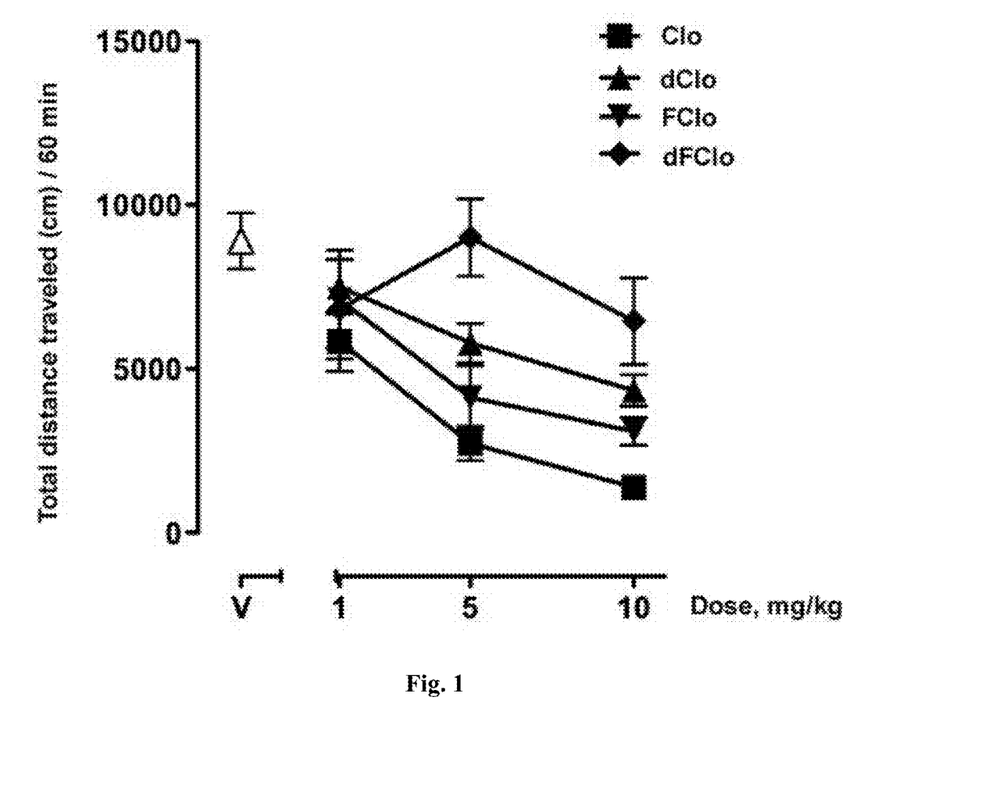
FIG. 1 provides a chart that illustrates curves reflecting the dependence of distance covered by the mice (n=8) after intake of different doses of clozapine (Clo), desmethylclozapine (dClo), fluoroclozapine (FClo) and desmethylfluoroclozapine (dFClo).

The results of in vitro experiments have been confirmed by the studies of sedation. Fluoroclozapine, desmethylfluoroclozapine, clozapine and desmethylclozapine were administered to CF-1 mice orally at doses of 1, 5 and 10 mg/kg (8 animals in each group). The total distance traveled by animals significantly reduced with the introduction of clozapine (FIG. 1), which indicated the sedation caused by medication. Sedation in case of introduction of fluoroclozapine was significantly lower. Desmethylfluoroclozapine at a dose of 10 mg/kg caused a negligible decrease in motor activity.

Thus, fluoroclozapine and desmethylfluoroclozapine cause a significantly lower sedation as compared to clozapine and desmethylclozapine.

Example 3

Reducing Sialorrhea

Intense salivation (sialorrhea) is a side effect of agonists of M4 muscarinic receptor. About 30% of patients taking (Ben-Aryeh, H. et. al., *Biol Psychiatry*, 1996, 39, 946-9) clozapine suffer from hypersalivation, which is one of the main reasons for patients to refuse to take the medication.

It is known that desmethylclozapine and analogues thereof bind to M1, M2, M3 receptors (application PCT/US2007/018201, Acadia Pharmaceuticals, Inc., publ. on Feb. 21, 2008). However, no binding of desmethylclozapine to M4 receptor was described.

Effect of fluoroclozapine (FClo), desmethylfluoroclozapine (dFClo), clozapine (Clo) and desmethylclozapine (dClo) on M4 muscarinic receptor was studied in functional experiments. The curves of dependence of functional response on the concentration of compounds for the receptor were made; the level of second messenger—cAMP determined according to the fluorescence after the lysis of cell expressing the receptor was taken as a criterion.

|    | Antagonism ($IC_{50}$, µM) | | | | Agonism ($EC_{50}$, µM) | | | |
|----|-------|-------|------|------|-------|-------|------|-------|
|    | dFClo | dClo  | FClo | Clo  | dFClo | dClo  | FClo | Clo   |
| M4 | >10   | >10   | 4.8  | 0.11 | 3.2   | 0.098 | 16   | 0.011 |

The studies have shown that fluorinated clozapine and desmethylclozapine, unlike their analogues, unexpectedly weakly bond to M4 receptors. The activating concentration of fluoroclozapine (16 µM) went beyond the therapeutically achievable concentrations; activating concentration of desmethylfluoroclozapine (3.2 µM) was 30 times higher than that of norclozapine.

Thus, unexpectedly weak interaction between fluoroderivatives with M4 muscarinic receptor presumably reduces the intensity of hypersalivation.

Example 4

Reducing the Risk of Occurrence of Extrapyramidal Disorders

Administration of antipsychotic drugs in many cases leads to development of irreversible neuroleptic-induced extrapyramidal disorders (EPR). The risk of occurrence of EPR correlates with the degree of blockade of D2 dopamine receptors (Knable, M. B. et. al., *Psychiatry Res*, 1997, 75, 91-101). The EPR occurrence is the most probable in patients taking classic neuroleptics (haloperidol, chlorpromazine) and some atypical antipsychotics (ziprasidone, risperidone) (Leucht, S. et. al., *Lancet*, 2013, 382, 951-62). Therefore, as the direct effect of antipsychotic drugs is targeted at D4 receptors of similar structure, the ratio of D4/D2 binding determines the therapeutic window of medication and the maximum tolerated dose.

Expanding the therapeutic window of medications due to changing the binding relationship with D4 and D2 receptors was a motivation for the development of antipsychotic drugs. The U.S. Pat. No. 5,538,965 discloses dopamine receptor ligands in which D4 receptor selectivity is increased due to the introduction of a bulky substituent in piperazine ring.

The therapeutic window for clozapine and fluoroderivatives thereof was estimated according to the ratio of binding constants (Kb) to D2 and D4 dopamine receptors, which were determined by IC50 values for the corresponding receptors in the set-up of antagonism. The response on cells expressing D2 receptors was determined according to the change in the cell conductibility induced by redistribution of intracellular calcium. For D4 receptor the level of second messenger—cAMP was taken as the criterion. The binding constants of quetiapine, olanzapine, risperidone, and haloperidol to D2 and D4 receptors were taken from ChemBL database (https://www.ebi.ac.uk/chembl/, accessed Jan. 15, 2014), geometric means of corresponding values were used.

|  | Kb (D2), μM | Kb (D4), μM | Therapeutic window (Kb, D2/Kb, D4) |
|---|---|---|---|
| Fluoroclozapine | 0.26 | 0.05 | 5.2 |
| Desmethylfluoroclozapine | 0.55 | 0.35 | 1.6 |
| Clozapine | 0.057 | 0.047 | 1.2 |
| Desmethylclozapine | 0.052 | 0.19 | 0.27 |
| Quetiapine | 0.2 | 1.78 | 0.11 |
| Olanzapine | 0.017 | 0.033 | 0.53 |
| Risperidone | 0.0027 | 0.01 | 0.28 |
| Haloperidol | 0.0021 | 0.0056 | 0.37 |

The table above shows that fluoroclozapine and desmethylfluoroclozapine have high D4-blocking activity with low D2-blocking activity.

Moreover, the comparison of data obtained by us with the similar data for the antipsychotic drugs of clinical use (see table) shows that the width of therapeutic window of fluoroderivatives of clozapine unexpectedly significantly exceeds other antipsychotics.

These data allow suggesting that the use of fluoroclozapine and desmethylfluoroclozapine will result in a decrease of the probability of EPR occurrence while maintaining antipsychotic activity.

Example 5

Eliminating Cognitive Disorders in Case of Schizophrenia

It is known that activation of M1 muscarinic receptor has a procognitive effect. Thus, agonists of M1 muscarinic receptor are studied in clinical trials for the elimination of cognitive disorders and modification of the course of Alzheimer's disease and (Fisher, A., *Neurotherapeutics*, 2008, 5, 433-42) schizophrenia (Shekhar, A. et. al., *Am J Psychiatry*, 2008, 165, 1033-9).

We have conducted functional studies of ability of fluoroclozapine and desmethylfluoroclozapine to activate M1 receptors. The activity was determined according to the fluorescence of Fluo-4 NW indicator introduced into cells induced by the change in Ca2+ ion concentration in the cytosol.

Figure 2:
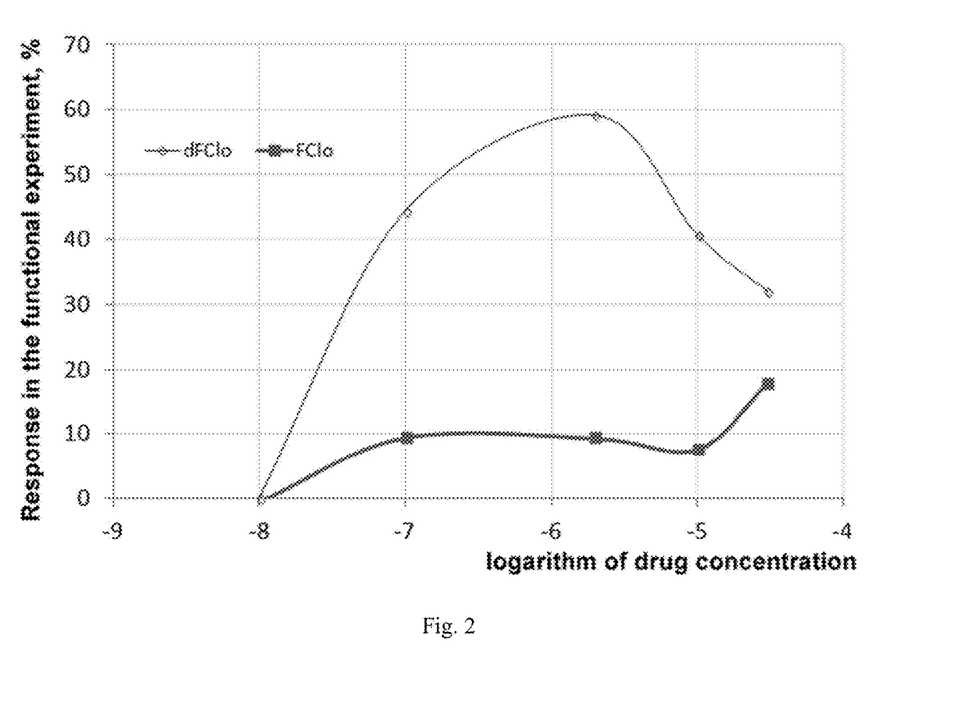
FIG. 2 provides a chart that illustrates curves reflecting the dependence of functional response (relative level of second messengers in cells) on the concentration of test compounds (dFClo—desmethylfluoroclozapine, FClo—fluoroclozapine) in an in vitro test system for M1 receptor.

The curves reflecting the dependence of functional response on the concentration for M1 receptor obtained by us show that desmethylfluoroclozapine is an agonist and causes a significant response in the therapeutic concentration range (FIG. 2). In the same experiment fluoroclozapine has shown virtually no effect on M1 receptors.

Figure 3:
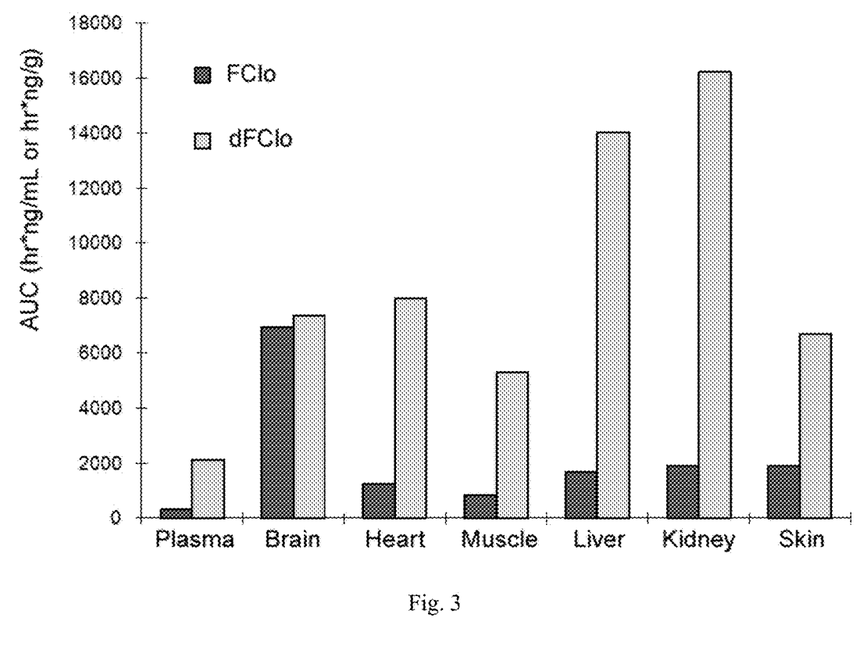
FIG. 3 provides a chart that illustrates the area under the "concentration-time" curve of fluoroclozapine (FClo) and desmethylfluoroclozapine (dFClo) in tissues and organs (plasma, brain, heart, muscles, liver, kidneys, skin) of Sprague Dawley rats (n=6) after single oral administration of fluoroclozapine at a dose of 10 mg/kg.

We have studied metabolism and distribution of fluoroclozapine in tissues. The concentration of fluoroclozapine and desmethylfluoroclozapine in tissues and organs (plasma, brain, heart, muscles, liver, kidneys, skin) of Sprague Dawley rats (n=6) was determined after single oral administration of fluoroclozapine at a dose of 10 mg/kg (FIG. 3). The studies of metabolism have shown that fluoroclozapine is metabolized to desmethylfluoroclozapine in rats, and that the concentrations of fluoroclozapine and its metabolite desmethylfluoroclozapine in the brain are consistent.

Thus, as it follows from experiments, after administration of fluoroclozapine its main metabolite is present in the brain at a concentration capable of causing the activation of muscarinic receptors, and fluoroderivatives of clozapine can be used for the treatment of cognitive disorders in case of schizophrenia.

Example 6

Antipsychotic Effect of Fluoroclozapine and Desmethylfluoroclozapine in In Vivo Experiments Antipsychotic effect of fluoroclozapine and desmethylfluoroclozapine was studied in experiments on prepulse inhibition of acoustic startle response. Prepulse inhibition (PPI) is inhibition of motor reaction to a sharp startling stimulus, generally acoustic, in the presence of a weak prestimulus. Prepulse inhibition is an indicator of sensor and motoric filtering, reflecting the ability of the CNS to filter out the sensory information. Reduction in prepulse inhibition is observed in case of schizophrenia and can be improved by intake of dopamine receptor agonists (apomorphine) or intake of NDMA antagonists (ketamine). The study of prepulse inhibition of acoustic startle response is a common test to determine the antipsychotic activity.

The activity of desmethylfluoroclozapine in the prepulse inhibition experiments was disclosed in patent RU 2441867 C2, publ. on Feb. 10, 2012 (Example 2). We conducted additional studies of antipsychotic properties of fluoroclozapine in the prepulse inhibition experiments using mice. On the day of the test animals received the test substance (clozapine or fluoroclozapine at doses of 5 and 10 mg/kg) and after 25 minutes—ketamine was administered intraperitoneally at a dose of 50 mg/kg. In 5 minutes after administration of ketamine animals were placed in chambers to determine the acoustic startle response. After adaptation during 5 minutes with white background noise of 65 dB, the mice were exposed to a set of six acoustic pulses of 120 dB during 40 ms with a mean interval of 15 seconds between pulses (interval from 7 to 23 seconds) in order to estimate the intensity of initial startle reflex.

In the next set of tests, the mice were randomly exposed to one of three effects:
a. prepulse with a duration of 20 ms and intensity of 4, 8, 12 and 15 dB, higher than the background noise (i.e., 69 dB, 71 dB, 77 dB, 81 dB), then, after 100 ms, noise pulse with intensity of 120 dB;
b. noise pulse with an intensity of 120 dB without any prepulse;
c. background noise without additional pulses.

Mice were exposed to each of effects 10 times. In the final set of tests mice were exposed to a set of six acoustic pulses of 120 dB during 40 ms.

The difference between the response to the first and last series of 6 acoustic pulses indicates habituation to the effect. Such habituation is a form of non-associative learning in which the response reduction is observed after a prolonged exposure. The intensity of the prepulse inhibition is calculated as follows:

$$\% \, PPI = 100\% * \frac{[(ACPb) - (ACPa)]}{(ACPb)},$$

where
ACPa—the total amplitude of acoustic startle reflex (ASR) after the a exposure. (prepulse and the main noise pulse)
ASRb—the amplitude of acoustic startle reflex after the b exposure (noise pulse without a prepulse)

Figure 4A:
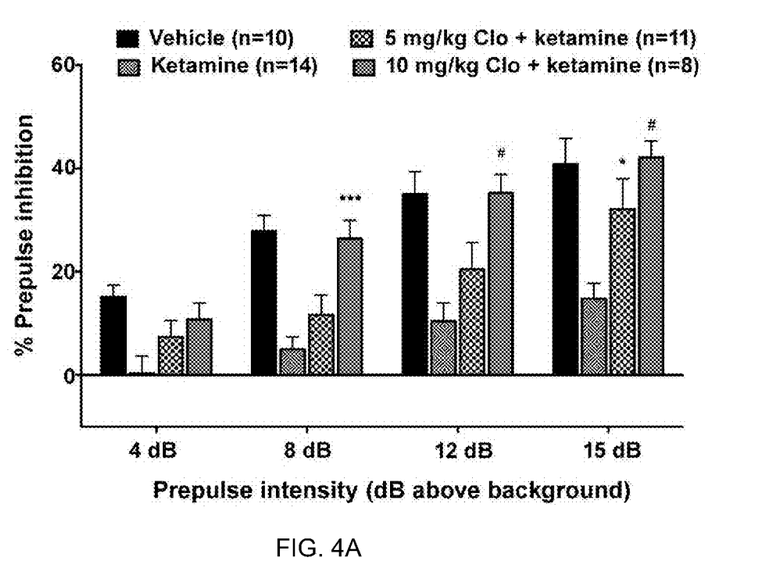
Figure 4B:
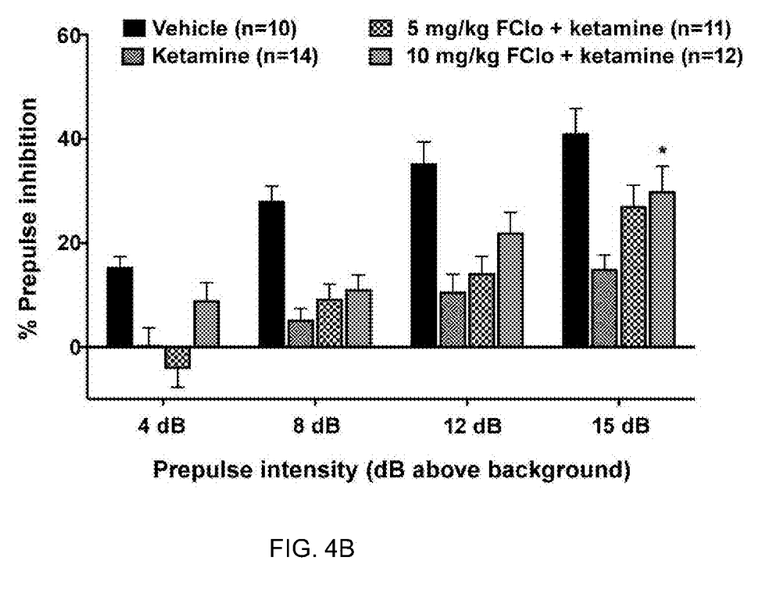

The results of the PPI experiments are shown in FIG. 4. According to the results of experiments, clozapine and fluoroclozapine demonstrated a statistically significant dose-dependent restoration of the PPI deficit caused by ketamine. Clozapine at a dose of 10 mg/kg completely restored the PPI. FClo activity at a dose of 10 mg/kg was comparable to clozapine activity at a dose of 5 mg/kg.

Thus, as it follows from experiments, antipsychotic effect of fluoroclozapine and desmethylfluoroclozapine is comparable to clozapine.

Example 7

Antihallucinatory Effect of Fluoroderivatives of Clozapine

It is known that the precursor of serotonin (5-oxytryptophan, 5-OT) causes a specific hyperkinesia in mice in the form of head-twitching with average duration of 30-60 minutes, which is explained by the activation of serotonergic system of the CNS. We have studied the effect of fluoroderivatives of clozapine on the severity of 5-oxytryptophan hyperkinesia suffered by mice. Each experimental group included 10 male mice weighing 20-22 g. The test substances were administered intragastrically at 1.0, 2.5, 5.0 and 10.0 mg/kg 30 minutes before the intraperitoneal administration of 5-oxytriptophan at a dose of 300 mg/kg. We counted the number of head twitches per 1 minute at intervals of 10 minutes during 60 minutes.

Figure 5:
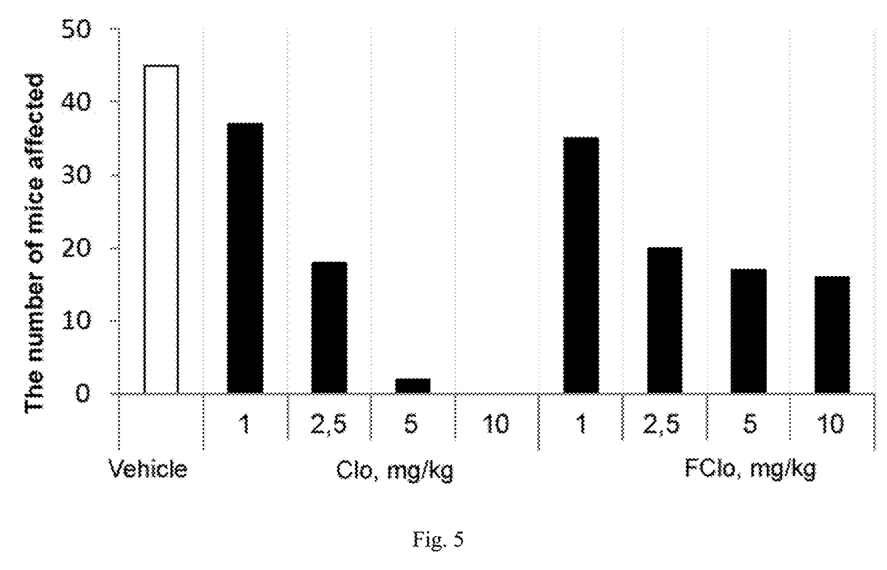
FIG. 5 provides a chart that illustrates the total number of animals with shaking under the effect of 5-oxytriptophan in experiments on antihallucinatory activity for different doses of clozapine (Clo) and fluoroclozapine (FClo).

Clozapine and fluoroclozapine demonstrated the most evident inhibition of twitches induced by administration of 5-OT (FIG. 5). The same effect of fluoroclozapine substance was observed when administered at doses ranging from 1.0 mg/kg to 10.0 mg/kg. The dose-dependent effect was observed at doses ranging from 1.0 mg/kg to 5.0 mg/kg, and then it steeped with a "plateau".

Thus, the data demonstrates that the test compounds have the central serotonin-blocking effect, which confirms their antihallucinatory effect.

In the course of further research of activity of fluoroclozapine and desmethylfluoroclozapine on a panel of therapeutically relevant G-protein-coupled receptors, we found a relatively weak activity in relation to the family of adrenergic receptors. In conjunction with the results of preliminary toxicological studies, the data indicates a reduction in the risk of autonomic dysfunctions, such as tachysystole, orthostatism, accommodation disorder, dysfunction of gastrointestinal tract and urination, weight gain, lack of coordination of muscle movements.

Figure 7:
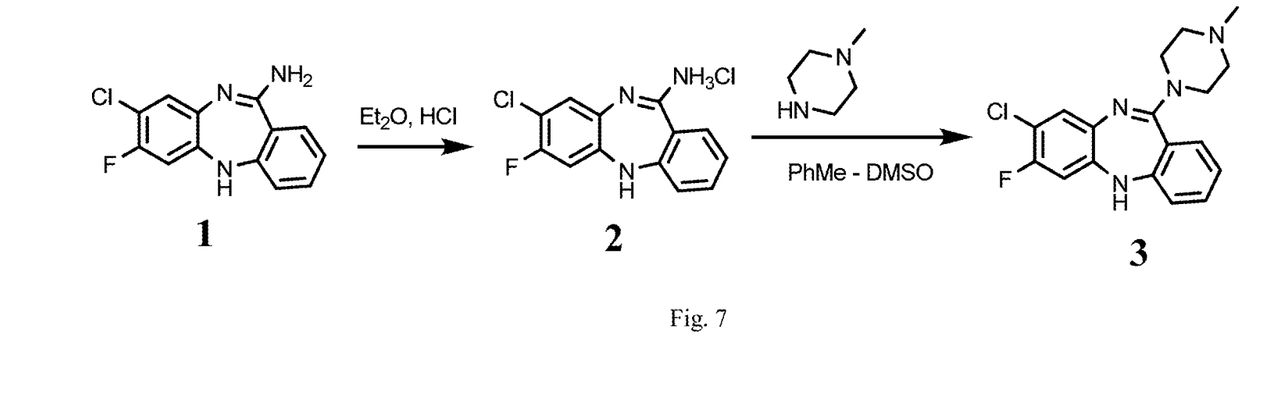
FIG. 7 is a reaction scheme that illustrates the synthesis of 11-(4-methyl piperazine-1-yl)-7-fluoro-8-chloro-5H-dibenzo[b,e][1,4]diazepine (fluoroclozapine) from 11-amino-7-fluoro-8-chloro-5H-dibenzo[b,e][1,4]diazepine.

Synthesis of Fluoroclozapine and Desmethylfluoroclozapine 11-(4-methyl piperazine-1-yl)-7-fluoro-8-chloro-5H-dibenzo[b,e][1,4]diazepine (fluoroclozapine) can be synthesized from 11-amino-7-fluoro-8-chloro-5H-dibenzo[b,e][1,4]diazepine as described below and illustrated by FIG. 7.

In a 2 l flat-bottomed flask equipped with a magnetic stir bar and a reflux condenser 64.9 g of compound 1 are added in 450 ml of diethyl ether. Then 124 ml of 3M HCl in dioxane are added to the resulting suspension. The reaction mass is stirred during 30 min. Crystals generated are then filtered, squeezed and washed on filter with two portions of diethyl ether of 150 ml each. Yield 2 is 73 g, which is 98% of theoretical yield.

98 g of compound 2 are dissolved in a mixture of toluene:DMSO=490:490 ml in a 2 l flat-bottomed flask equipped with a magnetic stir bar and a reflux condenser, then 291.7 ml of piperazine are added. The instrument is purged with argon, supply of inert gas from the cylinder is shut off (leaving the balloon filled with argon) and the reaction mass is boiled for 36 hours. TLC-control (dichloromethane:methanol=20:1).

The reaction mixture is poured into water and extracted with three portions of ethyl acetate of 150 ml each. The combined organic layer is washed with three portions of water of 150 ml each. The resultant product is dried over sodium sulfate and the solvent is removed using RFI. The distillation residue is mixed with 500 ml of methanol followed by stirring with the use of mechanical stirring device for 10 min. Crystals precipitated out are then filtered, squeezed on filter and washed on filter with 100 ml of methanol.

The product 3 is purified by recrystallization of methanol with activated charcoal, calculating the volume of solvent per 1 g of the product—15 ml of methanol and 10% of weight of compound 3 of the activated charcoal. Yield 3 is 59 g, which is 61%. $^1$H NMR (DMSO-$d_6$, 400 MHz) δ, ppm 2.198 (s, 3H, N—$CH_3$), 2.371 (br. s, 4H, 2 $CH_2$ piperazine), 3.286 (br. s, 4H, 2 $CH_2$ piperazine), 6.886 (d, 1H, J=10.4 Hz), 6.954 (d, 1H, J=8.0 Hz), 7.00-7.04 (m (d+t), 2H), 7.188 (d, 1H, J=8.0 Hz), 7.3-7.37 (m (s+t), 2H).

Figure 8:
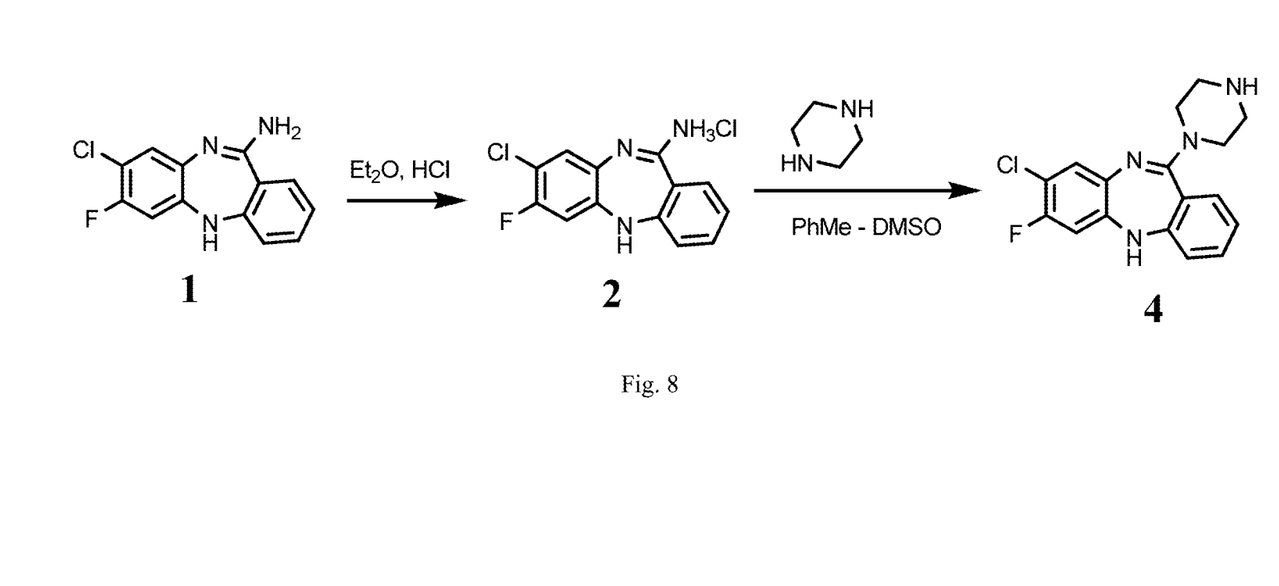
FIG. 8 is a reaction scheme that illustrates the synthesis of 11-(piperazine-1-yl)-7-fluoro-8-chloro-5H-dibenzo[b,e][1,4]diazepine (desmethylclozapine) from 11-amino-7-fluoro-8-chloro-5H-dibenzo[b,e][1,4]diazepine.

11-(piperazine-1-yl)-7-fluoro-8-chloro-5H-dibenzo[b,e][1,4]diazepine (desmethylclozapine) can be synthesized from 11-amino-7-fluoro-8-chloro-5H-dibenzo[b,e][1,4]diazepine as described below and illustrated by FIG. 8.

63 g of compound 2 is dissolved in a mixture of toluene:DMSO=315:315 ml in a 2 l flat-bottomed flask equipped with a magnetic stir bar and a reflux condenser, then 145.6 ml of piperazine are added. The instrument is purged with argon, supply of inert gas from the cylinder is shut off (leaving the balloon filled with argon) and the reaction mass is boiled for 36 hours. TLC-control (dichloromethane:methanol=20:1). The mixture is then cooled to indoor temperature and poured into 2 liters of water, with subsequent extraction with three portions of ethyl acetate of 200 ml each. The combined organic layers are washed with three portions of water of 100 ml each. The organic layer is dried over sodium sulfate.

The organic phase is filtered through a 10 mm silica gel bed and washed on filter with 2 liters of ethyl acetate. The mother liquor is extracted with 4M solution of hydrochloric acid in water, followed by washing of aqueous phase with three portions of ethyl acetate of 150 ml each.

Then, upon cooling, the aqueous phase is alkalized with initially cooled solution of 4M NaOH to adjust pH to 10. Crystals precipitated are filtered, squeezed and washed on filter with three portions of water of 150 ml each. The product 8 is recrystallized of toluene (ethanol, methyl ethyl ketone), calculating the volume of solvent: 3 ml of solvent per 1 g of product. Yield 4 is 45 g, which is 50% of theoretical yield. $^1$H NMR (DMSO-$d_6$, 400 MHz) δ, ppm 2.748 (br. s, 4H, 2 $CH_2$ piperazine), 3.225 (br. s, 4H, 2 $CH_2$ piperazine), 6.884 (d, 1H, J=10.4 Hz), 6.941 (d, 1H, J=8.0 Hz), 7.00-7.04 (m (d+t), 2H), 7.197 (d, 1H, J=8.0 Hz), 7.3-7.37 (m (s+t), 2H).

Examples of Pharmaceutical Compositions Containing Fluoroclozapine and Desmethylfluoroclozapine Fluoroclozapine and desmethylfluoroclozapine can be used as a substance or as a pharmaceutical composition. To prepare a pharmaceutical composition it is necessary to carefully mix an effective amount of a particular compound in the form of a pharmaceutically acceptable salt, solvate or hydrate, or in the form of free compounds, with a pharmaceutically acceptable carrier.

Non-limiting examples of pharmaceutically acceptable non-toxic salts include salts of amine group formed with inorganic acids, such as hydrochloric, hydrobromic, phosphoric, sulfuric and perchloric acid, or with organic acids, such as acetic, oxalic, maleic, tartaric, succinic or malonic acid, or formed by other methods used in the art, for example by means of ion exchange. Other pharmaceutically acceptable salts include adipate, alginate, ascorbate, aspartate, benzene sulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like.

The pharmaceutically acceptable carrier may be in various forms depending on the way of administration. It is desirable to prepare the pharmaceutical compositions in a single dosage form, preferably suitable for oral or parenteral administration. In preparing the compositions it is allowed to use any carriers known in pharmaceutics, such as water, glycols, oils, alcohols and similar agents, starches, sugars, kaolin, povidone, silicon dioxide, magnesium stearate, talc, lubricants, binding-agents, facilitating the disaggregation of dosage form, and the like. In case of compositions for parenteral administration, the carrier will usually contain sterile water, at least for the most part, although other ingredients can be included to achieve solubility. For example, it is possible to prepare solutions for injection, in which the carrier contains physiological salt solution, glucose solution or neutral oils.

Typically, the compound is administered to patients in need of treatment at a daily dosage of about 25 mg to 7,000 mg per patient, preferably 100 to 300 mg per patient. The amount of compound, which will be effective in the treatment or prevention of a particular disorder or condition, will depend, in particular, on a number of well-known factors that influence the effective dosage of medications. Dose-ranging may be individual, starting with the prescription of small doses (25 mg) with gradual dose escalation until achieving a therapeutic effect.

Pharmaceutical compositions developed in this invention may be administered once or multiple times at intervals, for example, 1 to 4 times per day. It shall be understood that the exact dosage, regime and duration of treatment may vary depending on age, weight and condition of a patient being treated, and may be determined empirically using any of known test protocols or through the extrapolation of the data of in vivo or in vitro tests, or of the diagnostic data. It shall be further understood that any specific dosage regimes for any particular individual shall be adjusted over time according to the individual need and professional judgment of a specialist, administering or responsible for the administration of medications.

In addition it shall be understood that the specific dose level and frequency of administration for any particular patient may vary and depends on factors, including activity of the specific compound applied, age, body weight, general health condition, sex, diet, route of administration, drug combination, and severity of a particular condition.

The following compositions illustrate the possible, but non-limiting examples of medications containing fluoroclozapine and desmethylfluoroclozapine:

Tablet 1

| | |
|---|---|
| Fluoroclozapine | 100 mg |
| Corn starch | 60.4 mg |
| Lactose monohydrate | 190.0 mg |
| Kollidon 30 | 17.1 mg |
| Aerosil A-300 | 3.8 mg |
| Magnesium stearate | 1.1 mg |
| Talc | 7.6 mg |

Tablet 2

| | |
|---|---|
| Desmethylfluoroclozapine citrate | 300 mg |
| Corn starch | 181.2 mg |
| Lactose monohydrate | 380.0 mg |
| Kollidon 30 | 51.3 mg |
| Aerosil A-300 | 11.4 mg |
| Magnesium stearate | 3.3 mg |
| Talc | 15.2 mg |

Solution for Injection

| | |
|---|---|
| Desmethylfluoroclozapine | 50 mg |
| Hydroxyanisole | 0.5 mg |
| Lauric acid | 0.5 mg |
| Vegetable oil | 2 mg |

Capsule 1

| | |
|---|---|
| Fluoroclozapine | 100 mg |
| Corn starch | 120.2 mg |
| Povidone | 94 mg |
| Magnesium stearate | 50 mg |
| Talc | 8 mg |

Thus, as it follows from our experiments, it has unexpectedly been found that fluoroclozapine and desmethylfluoroclozapine, unlike other compounds having antipsychotic activity, known from the prior art, not only have the efficacy which is equal to (and in some cases even better than) clozapine, the only neuroleptic officially recommended for use in case of resistance to other antipsychotics, but also demonstrate a significantly lower probability of occurrence of side effects involved by clozapine (and even by many other antipsychotic drugs), including sedation, tachycardia, orthostatism, agranulocytosis and hypersalivation.

This brings us to the conclusion that these compounds can be used to develop an effective medication, the use of which in treatment of treatment-resistant forms of schizophrenia allows for eliminating both positive symptoms of schizophrenia (including delusion, auditory hallucinations, thought disorder) and its negative symptoms (including flat affect, poverty of speech) and cognitive disorders, and the use of which does not cause severe side effects that limit its use, including sedation, tachycardia, orthostatism, agranulocytosis and hypersalivation.

The invention claimed is:

1. A method of treating a treatment-resistant form of schizophrenia, comprising:
   administering a therapeutically effective amount of a pharmaceutical composition to a subject in need thereof, wherein the pharmaceutical composition comprises an active ingredient selected from the group consisting of: (a) 11-(piperazine-1-yl)-7-fluoro-8-chloro-5H-dibenzo[b,e][1,4]diazepine; (b) 11-(4-methyl piperazine-1-yl)-7-fluoro-8-chloro-5H-dibenzo

[b,e][1,4]diazepine; and (c) a pharmaceutically acceptable salt, hydrate, or solvate of (a) or (b); and reducing one or more symptoms associated with schizophrenia, wherein said symptoms comprise symptoms of a cognitive disorder;

wherein the therapeutically effective amount comprises a daily dosage of 50 to 300 mg of the active ingredient.

2. The method of claim 1, wherein the treatment-resistant schizophrenia is a paranoid, disorganized, catatonic, undifferentiated or residual type of schizophrenia, schizophreniform disorder, schizoaffective disorder or a schizotypal disorder.

3. The method of claim 1, wherein the treatment-resistant schizophrenia is defined as a schizophrenia which does not display symptomatic remission, an expected therapeutic response, or which displays at least one severe side effect, as a result of a previous therapeutic treatment.

4. The method of claim 3, wherein the at least one severe side effect is selected from the group consisting of: agranulocytosis, sedation, cognitive disorders, disorders of attention or of different aspects of memory, manifestations of autonomic dysfunction, tachysystole, orthostatism, accommodation disorder, dysfunction of gastrointestinal tract and urination, weight gain, behavioral toxicity, lack of coordination of muscle movements, absent-minded behavior, drowsiness episodes, and sialorrhea.

5. The method of claim 1, wherein the therapeutically effective amount comprises a daily dosage of about 300 mg.

6. The method of claim 1, wherein the active ingredient in the pharmaceutical composition is 11-(piperazine-1-yl)-7-fluoro-8-chloro-5H-dibenzo[b,e][1,4]diazepine, or a pharmaceutically acceptable salt, hydrate or solvate thereof.

7. The method of claim 1, wherein the active ingredient in the pharmaceutical composition is 11-(4-methyl piperazine-1-yl)-7-fluoro-8-chloro-5H-dibenzo[b,e][1,4]diazepine, or a pharmaceutically acceptable salt, hydrate or solvate thereof.

8. The method of claim 1, wherein the pharmaceutical composition is administered to the patient at a dosage comprising 1.0 to 10.0 mg/kg of the active ingredient.

* * * * *